US008647283B2

(12) United States Patent
Matsumoto et al.

(10) Patent No.: US 8,647,283 B2
(45) Date of Patent: Feb. 11, 2014

(54) PULSE ABNORMALITY DETECTING DEVICE

(75) Inventors: Hiroshi Matsumoto, Tokyo (JP); Kazuko Komatsu, Tokyo (JP)

(73) Assignee: The Matsumoto Institute of Leading Edge of Technology Ltd., Tokyo (JP)

( * ) Notice: Subject to any disclaimer, the term of this patent is extended or adjusted under 35 U.S.C. 154(b) by 279 days.

(21) Appl. No.: 12/736,837

(22) PCT Filed: Jul. 17, 2008

(86) PCT No.: PCT/JP2008/063325
§ 371 (c)(1),
(2), (4) Date: Nov. 15, 2010

(87) PCT Pub. No.: WO2009/139083
PCT Pub. Date: Nov. 19, 2009

(65) Prior Publication Data
US 2011/0066049 A1    Mar. 17, 2011

(30) Foreign Application Priority Data

May 16, 2008   (JP) .................................. 2008-129268

(51) Int. Cl.
*A61B 5/024*   (2006.01)
(52) U.S. Cl.
USPC ............................ 600/503; 600/502; 600/500
(58) Field of Classification Search
USPC ................................................ 600/500–507
See application file for complete search history.

(56) References Cited

U.S. PATENT DOCUMENTS

| 3,838,684 | A | * | 10/1974 | Manuel et al. | 600/503 |
| 4,185,621 | A | * | 1/1980 | Morrow | 600/485 |
| 6,132,383 | A | * | 10/2000 | Chesney et al. | 600/502 |
| 6,334,850 | B1 | * | 1/2002 | Amano et al. | 600/500 |
| 6,432,060 | B1 | * | 8/2002 | Amano | 600/490 |
| 6,491,647 | B1 | * | 12/2002 | Bridger et al. | 600/585 |

(Continued)

FOREIGN PATENT DOCUMENTS

| JP | 49-72089 | U | | 6/1974 | |
| JP | 05-052975 | A | | 3/1993 | |
| JP | 05052975 | A | * | 3/1993 | G04G 1/00 |

(Continued)

OTHER PUBLICATIONS

International Search Report dated Aug. 19, 2008, issued for PCT/JP2008/063325.

*Primary Examiner* — Navin Natnithithadha
*Assistant Examiner* — Meredith Weare
(74) *Attorney, Agent, or Firm* — Edwards Wildman Palmer LLP; James E. Armstrong, IV; Edmund J. Koundakjian

(57) ABSTRACT

A pulse abnormality detecting device comprises a band attached to a wrist, a first sliding member with which the band is armored and which slides in the circumference direction of the band along the band, a second sliding member which is slidably provided on the first sliding member and which slides in the axis direction of the band, a pulse sensor which is provided on the second sliding member and which is provided in such a manner that the position of the sensor can be adjusted to the inner side or the side of the band, and a pulse abnormality detecting unit for detecting the abnormality of the pulse from the output data of the pulse sensor. The device can accurately detect the pulse of a user with high precision, adapting to a personal difference.

15 Claims, 4 Drawing Sheets

(56) References Cited

U.S. PATENT DOCUMENTS

| | | | | |
|---|---|---|---|---|
| 7,306,563 | B2 * | 12/2007 | Huang | 600/500 |
| 2005/0010119 | A1 * | 1/2005 | Palti et al. | 600/499 |
| 2005/0065442 | A1 * | 3/2005 | Hashimoto et al. | 600/501 |
| 2006/0047207 | A1 * | 3/2006 | Itonaga et al. | 600/500 |
| 2007/0191718 | A1 * | 8/2007 | Nakamura | 600/503 |
| 2008/0058622 | A1 * | 3/2008 | Baker | 600/344 |

FOREIGN PATENT DOCUMENTS

| | | |
|---|---|---|
| JP | 2002-028140 A | 1/2002 |
| JP | 2005-156531 A | 6/2005 |
| JP | 2007-215749 A | 8/2007 |

* cited by examiner (a)

(b)

(c)

# PULSE ABNORMALITY DETECTING DEVICE

TECHNICAL FIELD

The present invention relates to pulse abnormality detection apparatuses for detecting pulse abnormalities of users.

BACKGROUND ART

Examples of pulse abnormality detection apparatuses for detecting pulse abnormalities of users include a medical watch disclosed in Patent Document 1 (Japanese Unexamined Patent Application Publication No. 5-52975). In the medical watch, a pulse sensor is fixed at a given position inwardly of a wristwatch band so as to be brought into intimate contact with a position at which a pulsation of a wrist wearing the medical watch is detectable, a temperature sensor for detecting a body temperature is fixed at a given position inwardly of the wristwatch band, and outputs of these sensors are supplied to a controller. The controller compares an output waveform from the pulse sensor with a standard waveform, stored in advance, to perform blinking display on a display module and/or issue an alarm when the comparison result falls outside an allowable range defined by a set value, and also compares output data from the temperature sensor with a set value to perform blinking display on the display module and/or issue an alarm when the comparison result falls outside an allowable range defined by the set value. Furthermore, the medical watch is formed so that a transmitter-receiver transmits a signal for issuing an alarm to a master unit to give an alarm from the master unit, and receives identification data or hospital data from the master unit to store the data in such a manner that the data is displayable on the display module.

DISCLOSURE OF THE INVENTION

Actually, in the medical watch disclosed in Patent Document 1, the pulse sensor is merely fixed at a position inwardly of the band so as to be brought into intimate contact with a position at which a pulsation of the wrist is detectable, and a specific fixation position of the pulse sensor is unknown; however, a position at which the pulse sensor is set is extremely important in order to detect a pulse at a practical level. Specifically, since a wrist has two large arteries such as a radial artery and an ulnar artery, pulses of both of radial and ulnar arteries are detected if the pulse sensor is merely placed at a position at which a pulsation of the wrist is simply detectable, and frequency change and/or phase change are/is caused in detected pulses, thus making it difficult to accurately detect pulses. Moreover, since an optimal position for detecting a pulse is different among individuals, the pulse sensor is also required to be provided at an optimal position in accordance with individual differences.

The present invention has been proposed in view of the above-described problems, and its object is to provide a pulse abnormality detection apparatus capable of accurately detecting a user's pulse with high precision while adapting to individual differences.

A pulse abnormality detection apparatus according to the present invention includes: a band worn around a wrist or an arm; a pulse sensor provided inwardly or laterally of the band; and a pulse abnormality detector for detecting a pulse abnormality from data outputted from the pulse sensor, wherein the pulse sensor is provided so that its position is adjustable.

Another aspect of the present invention provides a pulse abnormality detection apparatus including: a storage module for storing a standard pulse waveform and a set value by which a pulse allowable range is defined; and a pulse abnormality recognition module for making a comparison between an output waveform, which is data outputted from the pulse sensor, and the standard pulse waveform, and for recognizing an abnormality when results of the comparison include a value falling outside the allowable range defined by the set value, wherein the pulse abnormality detector is formed by the storage module and the pulse abnormality recognition module.

Still another aspect of the present invention provides a pulse abnormality detection apparatus, wherein the pulse sensor is provided so as to be movable or slidable in a circumferential direction of the band and in an axial direction of the band.

Yet another aspect of the present invention provides a pulse abnormality detection apparatus including: a first slide body that is externally attached to the band and that slides along the band; and a second slide body that is slidably provided at the first slide body and that slides in the axial direction of the band, wherein the second slide body is provided with the pulse sensor.

Still yet another aspect of the present invention provides a pulse abnormality detection apparatus, wherein the second slide body has elasticity by which the pulse sensor is urged inwardly of the band, or an elastic member, by which the pulse sensor is urged inwardly of the band, is provided between the second slide body and the pulse sensor.

Another aspect of the present invention provides a pulse abnormality detection apparatus, wherein the elastic member is a pressure sensitive diaphragm.

Still another aspect of the present invention provides a pulse abnormality detection apparatus, wherein a tip of the second slide body is provided with a fixation member having a shape substantially conforming to at least part of a circumference of the wrist or that of the arm, or a fixation member deformable into the shape.

Yet another aspect of the present invention provides a pulse abnormality detection apparatus, wherein the band is provided with a main body, and the main body is provided with the pulse abnormality detector.

Still yet another aspect of the present invention provides a pulse abnormality detection apparatus, wherein the band is provided with a transmitter, a receiving terminal is provided with the pulse abnormality detector, and an output waveform, which is data outputted from the pulse sensor, is transmitted to the receiving terminal via the transmitter.

In the pulse abnormality detection apparatus according to the present invention, the pulse sensor is provided inwardly or laterally of the band so that the position of the pulse sensor is adjustable, thus allowing each user to accurately place the pulse sensor at a position at which neither frequency change nor phase change is caused in detected pulses, i.e., at a position corresponding to a single artery such as a radial artery or an ulnar artery, and to accurately detect a single artery wave. Accordingly, it is possible to accurately detect the user's pulse or pulse waveform with high precision while adapting to individual differences, and it is also possible to accurately calculate various parameters based on the pulse or pulse waveform.

Further, the standard pulse waveform and the set value by which the pulse allowable range is defined are stored, a comparison is made between an output waveform, which is data outputted from the pulse sensor, and the standard pulse waveform, and an abnormality is recognized when results of the comparison include a value falling outside the allowable range defined by the set value, thus making it possible to accurately detect a pulse abnormality with a simple and low-cost structure.

Furthermore, the pulse sensor is provided so as to be movable in the circumferential direction and axial direction of the band, thus making it possible to easily adjust the position of the pulse sensor to a position corresponding to a single artery by utilizing the direction of the band along the circumference of the wrist or that of the arm.

Moreover, the first slide body is externally attached to the band so as to be slid along the band, the second slide body is provided at the first slide body so as to be slidable in the axial direction of the band, and the second slide body is provided with the pulse sensor; thus, the band can be effectively utilized for a moving operation in the circumferential of the band, and fine control in the circumferential direction and axial direction of the band can be realized by sliding movement. In addition, a moving means for the pulse sensor can be formed with a simple structure at a low cost.

Besides, the second slide body has elasticity by which the pulse sensor is urged inwardly of the band, or the elastic member, by which the pulse sensor is urged inwardly of the band, is provided between the second slide body and the pulse sensor; thus, the pulse sensor, which has been adjusted to a position suitable for detection of a pulse of the wrist or arm, can be reliably abutted against the wrist or arm, and the user's pulse can be more stably detected.

Further, the elastic member is a pressure sensitive diaphragm; thus, the pulse sensor can be more reliably abutted against a position suitable for detection of a pulse of the wrist or arm, excessive compression of a blood vessel, which will be caused by the pulse sensor and will distort a pulse waveform, can be prevented, and more accurate pulse detection can be ensured.

Furthermore, the tip of the second slide body is provided with the fixation member having a shape substantially conforming to at least part of the circumference of the wrist or that of the arm, or the fixation member deformable into the shape; thus, the second slide body and the pulse sensor can be fixed at optimal positions to prevent positional deviations thereof, and more stable pulse detection can be ensured.

Moreover, the main body of the band is provided with the pulse abnormality detector; thus, a pulse abnormality can be recognized by the main body of the band, and the user wearing the band, for example, can recognize a pulse abnormality on the spot.

Besides, the band is provided with the transmitter, the receiving terminal is provided with the pulse abnormality detector, and an output waveform from the pulse sensor is transmitted to the receiving terminal via the transmitter, thereby allowing the user himself or herself or other people such as family and doctors to recognize, on a larger display screen or the like of the receiving terminal, a pulse abnormality with the use of the receiving terminal such as a mobile phone, an on-vehicle terminal or a personal computer, for example, for receiving data from the pulse sensor.

BEST MODE FOR CARRYING OUT THE INVENTION

Hereinafter, embodiments of pulse abnormality detection apparatuses according to the present invention will be described with reference to the drawings.

[Pulse Abnormality Detection Apparatus of First Embodiment]

Figure 1:
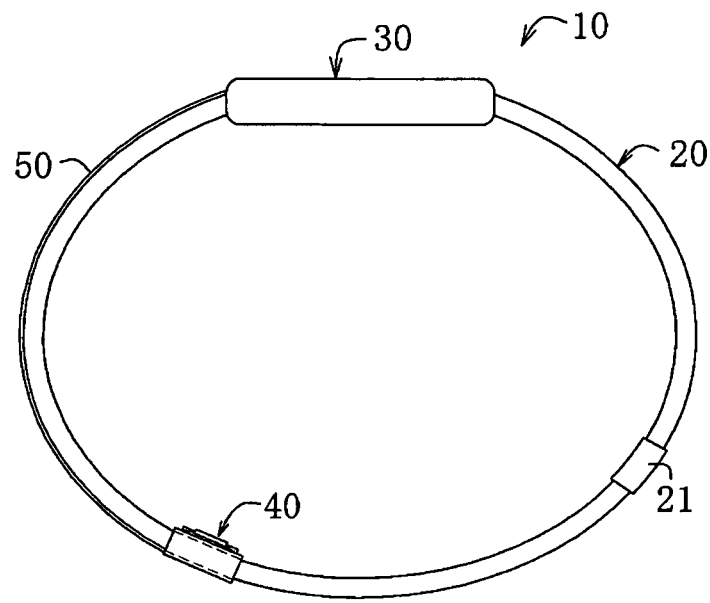
FIG. 1 is a front view of a pulse abnormality detection apparatus according to a first embodiment.

As illustrated in FIG. 1, a pulse abnormality detection apparatus 10 according to a first embodiment includes: a substantially annular strap-like band 20 worn around a user's wrist with the use of a connection made by an attachable/detachable connector 21; a main body 30 which is provided so as to be attached to the band 20 and in which a pulse abnormality detector is contained; a sensor means 40 provided so as to be slidable along the band 20; and a connection line 50 for establishing an electric connection between the main body 30 and a pulse sensor 43 of the sensor means 40.

Figure 2:
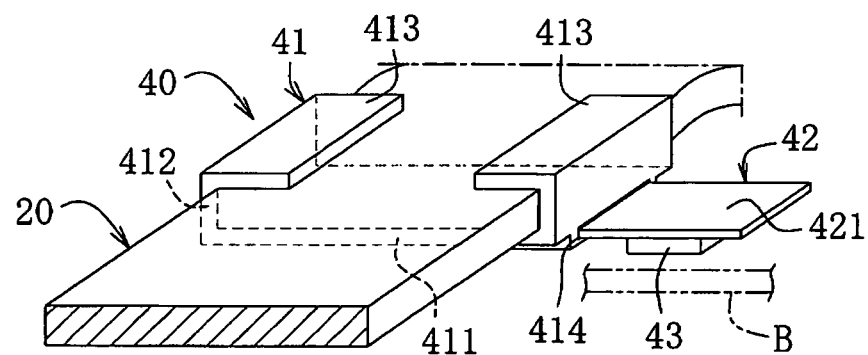
FIG. 2 is a partial perspective view illustrating a periphery of a sensor means of the pulse abnormality detection apparatus according to the first embodiment.
Figure 3:
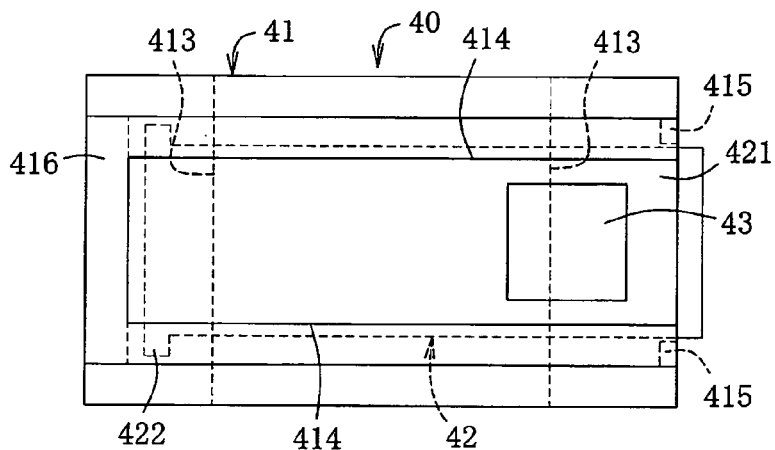
FIG. 3 is a bottom view illustrating the sensor means of the pulse abnormality detection apparatus according to the first embodiment.

As illustrated in FIGS. 2 and 3, the sensor means 40 has: a first slide body 41 that is externally attached to the band 20 and that slides along the band 20; a second slide body 42 that is slidably provided at the first slide body 41 and that slides in an axial direction of the band 20; and the pulse sensor 43 provided on the second slide body 42.

The first slide body 41 is approximately C-shaped when viewed from the front and has: an inner wall 411 provided along an inner face of the band 20; lateral walls 412, 412 outwardly located and vertically provided at both sides of the inner wall 411; and outside pieces 413, 413 extended inward from outer ends of the lateral walls 412, 412, so that the first slide body 41 is provided so as to be slidable while being wrapped around the band 20. At the inner wall 411 of the first slide body 41, a pair of rail parts 414, 414 extending in the axial direction of the band 20 are formed, and each rail part 414 is approximately L-shaped in cross section. One end portions of the rail parts 414 face an opening, inwardly protruding engaged parts 415 are provided inwardly in the vicinity of the opening, and the other end portions of the rail parts 414 are closed to provide a closed part 416.

The second slide body 42 has: an approximately rectangular base plate 421; and an engagement piece 422 formed so as to be protruded outward from both lateral faces of an end portion of the base plate 421, which is located adjacent to the closed part 416 of the rail parts 414. The base plate 421 is inserted between the pair of rail parts 414, 414 of the first slide body 41, and regions of the base plate 421, which are located in the vicinity of both lateral end portions thereof, are slidable inside the rail parts 414, 414 together with the engagement piece 422. The base plate 421 is slidable between a position at which a front end of the engagement piece 422 abuts against the engaged parts 415 of the rail parts 414 and a position at which a rear end of the base plate 421 abuts against the closed part 416. The second slide body 42 or the base plate 421 is preferably made of an elastic material or a center portion thereof preferably has an elastic shape such as an inwardly convexly curved shape, and the pulse sensor 43 can be urged inwardly of the band 20 by providing the elastic second slide body 42.

The pulse sensor 43 is disposed close to an end portion of the base plate 421 of the second slide body 42, which corresponds to the opening side of the rail parts 414, and is fixed to the inner face side of the base plate 421. Specifically, the pulse sensor 43 is provided so to be movable between a region located inwardly of the band 20 and a region protruded laterally from the band 20, provided so as to be movable in a circumferential direction of the band 20 in accordance with a movement of the first slide body 41 along the band 20, and provided so as to be movable in the axial direction of the band 20 in accordance with a movement of the second slide body 42 with respect to the first slide body 41.

The pulse sensor 43 is electrically connected to the main body 30 via the connection line 50 (partially not illustrated) located along a circumference of the band 20. Note that the main body 30 maybe provided with an extending/retracting means having, for example, a structure in which a rotation means of a retrieving roll for retrieving the connection line 50 is controlled by a switch, thereby allowing the connection line 50 to be extensible and retractable. Further, as the pulse sensor 43, a pressure sensor for measuring a pulse pressure of a blood vessel is used in the present example, but a photoplethysmographic instrument for measuring a light quantity change resulting from a change in hemoglobin responsive to heartbeat, for example, may be used, or an appropriate pulse sensor such as an acceleration sensor, an ultrasonic sensor, a photoplethysmographic sensor or an optical displacement sensor may be used when necessary in the present invention.

Figure 4:
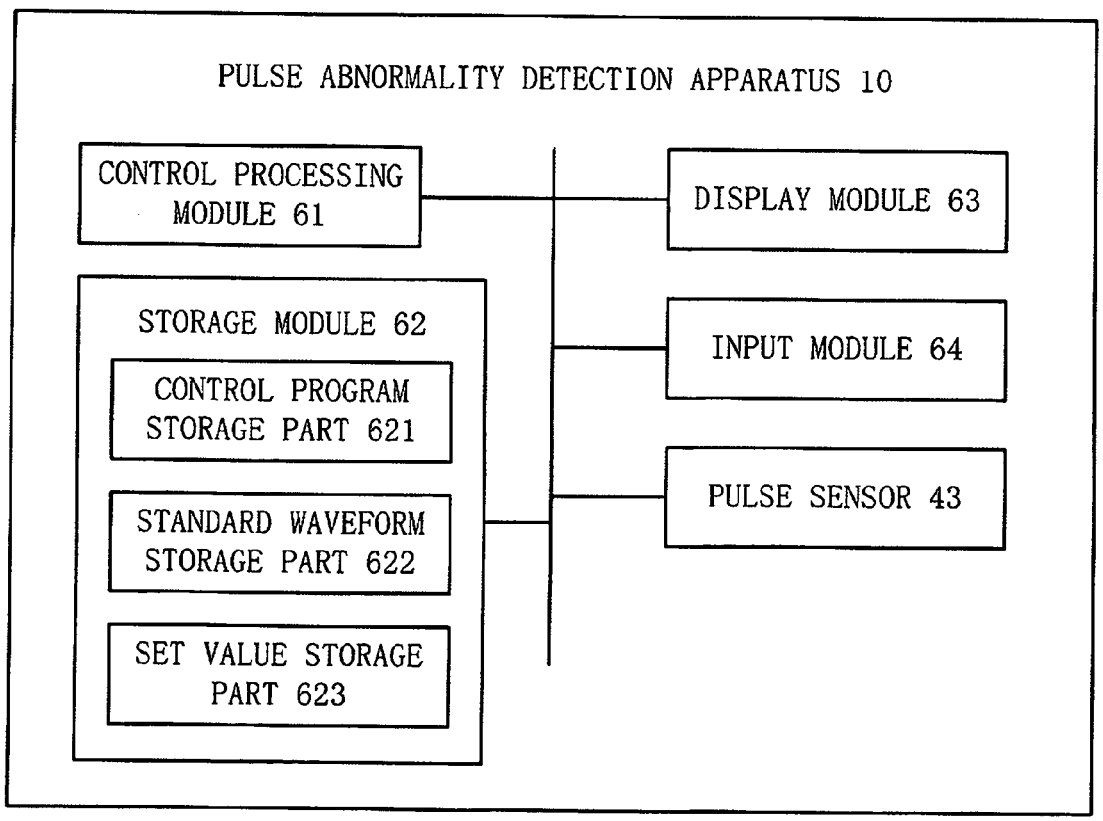
FIG. 4 is a block diagram illustrating a hardware configuration of the pulse abnormality detection apparatus according to the first embodiment.

As illustrated in FIG. 4, the main body 30 includes: a control processing module 61 including a CPU, a memory, etc.; a storage module 62 including a small HDD, an EEPROM or the like; a display module 63 such as a liquid crystal display or an organic EL display; and an input module 64 including a data input part through which data to be stored in the storage module 62 is inputted, an operational input part through which an operational input is performed on the main body 30, etc. The storage module 62 has: a control program storage part 621 for storing a control program for pulse abnormality detection processing; a standard waveform storage part 622 for storing a standard pulse waveform; and a set value storage part 623 for defining a pulse allowable range for each detection item. Note that the control processing module 61 and the storage module 62 correspond to the pulse abnormality detector.

A standard pulse waveform, which is stored in the standard waveform storage part 622, may be a standard waveform of an ordinary person in a normal state, but a standard waveform of a user himself or herself in a normal state, for example, may alternatively be stored. When the standard waveform of the user himself or herself is stored, the pulse abnormality detection apparatus 10, for instance, is allowed to switch between a setting mode and a use mode in response to a switching input through the input module 64, and is formed, for example, so that the pulse abnormality detection apparatus 10 is put in the setting mode by the input module 64, a waveform of a pulse is measured for a given period of time by the pulse sensor 43, the measured waveform is stored as the standard waveform in the standard waveform storage part 622 by the control processing module 61, and then the pulse abnormality detection apparatus 10 is switched to the use mode when it is used.

The control processing module 61 captures an output waveform from the pulse sensor 43, reads, in accordance with the control program stored in the control program storage part 621, the standard pulse waveform from the standard waveform storage part 622 while reading, from the set value storage part 623, set values by which the pulse allowable range is defined, makes a comparison between the output waveform from the pulse sensor 43 and the standard pulse waveform, recognizes an abnormality when results of the comparison include a value falling outside the allowable range defined by the set values, and displays, on the display module 63, a detection item for which an abnormality is recognized and a message saying that an abnormality is caused.

When the pulse abnormality detection apparatus 10 according to the first embodiment is used, the user detaches the connector 21 to place the band 20 around his or her wrist, and then attaches the connector 21 to wear the band 20 around his or her wrist. The first slide body 41 is slid along the band 20 to place the first slide body 41 at a position substantially corresponding to a radial artery B; furthermore, the second slide body 42 is slid in the axial direction of the substantially annular band 20 by sliding the second slide body 42 with respect to the first slide body 41, and the pulse sensor 43 mounted on the second slide body 42 is placed at a position at which the radial artery B is located closer to a superficial layer of the wrist and which is suitable for obtainment of a pulse, thereby abutting the pulse sensor 43 against a position suitable for obtainment of a pulse of the radial artery B. In this case, when the elastic second slide body 42 has elasticity, the pulse sensor 43 is urged inward due to the elasticity, and the pulse sensor 43 is more reliably abutted against the position suitable for the obtainment of a pulse.

Then, the main body 30 is started up in response to an input through the input module 64, and the pulse sensor 43 is started up in response to the startup of the main body 30. The pulse sensor 43 continuously measures pulse pressures of the radial artery B of the user, and outputs, to the control processing module 61, an output waveform of pulses which is indicative of a temporal change in the pulse pressures. The control processing module 61 continuously captures the output waveform of pulses from the pulse sensor 43, compares the standard pulse waveform, read from the standard waveform storage part 622, with the output waveform of the pulses, and obtains a given value such as a peak value interval of the pulses, which is equivalent to an R-R interval of an electrocardiogram, for example. Moreover, the obtained given value is compared with set values which are read from the set value storage part 623 and by which an allowable range including a set upper limit value and a set lower limit value of the pulse peak value interval is defined; thus, when the obtained given values include a value falling outside the allowable range, e.g., when the obtained peak value interval exceeds the set upper limit value or falls below the set lower limit value, an abnormality is recognized, and a detection item such as "Irregular Pulse" for which an abnormality is recognized and a message saying that an abnormality such as "Danger" is caused are displayed on the display module 63.

In the pulse abnormality detection apparatus 10 according to the first embodiment, the pulse sensor 43 is provided so that its position is adjustable; thus, each user can accurately place the pulse sensor 43 at a position corresponding to the radial artery B at which neither frequency change nor phase change is caused in detected pulses, making it possible to accurately detect the user's pulse with high precision while adapting to individual differences. Further, a pulse abnormality is recognized by comparison with the standard pulse waveform, thereby making it possible to detect a pulse abnormality with a simple and low-cost processing structure. Furthermore, the band 20 can be effectively utilized for a moving operation in the band circumferential direction and fine control in the band circumferential direction and axial direction can be easily realized by sliding the first slide body 41 and the second slide body 42. Moreover, a moving means for the pulse sensor 43 can be formed with a simple structure at a low cost. Besides, the pulse abnormality detector is provided in the main body 30 of the band 20, thereby allowing the user wearing the band 20 to recognize a pulse abnormality on the spot. In addition, when the second slide body 42 is formed to have elasticity, the pulse sensor 43 is allowed to abut against the wrist with reliability, and to more stably detect the user's pulse.

[Pulse Abnormality Detection Apparatus of Second Embodiment]

A pulse abnormality detection apparatus 10 according to a second embodiment has a structure similar to that of the pulse abnormality detection apparatus illustrated in FIG. 1, and thus has: a substantially annular strap-like band 20 worn around a user's wrist with the use of a connection made by an attachable/detachable connector 21; a main body 30 provided so as to be attached to the band 20; a sensor means 40 provided so as to be slidable along the band 20; and a connection line 50 for establishing an electric connection between the main body 30 and a pulse sensor 43 of the sensor means 40. However, a pulse abnormality detector is not provided in the main body 30, and a receiving terminal 70, wirelessly communicably connected to the pulse abnormality detection apparatus 10 or the main body 30, is provided with a control processing module 71 and a storage module 72 which correspond to the pulse abnormality detector (see FIG. 5). Note that components, which are not particularly mentioned in the second embodiment, are similar to those of the first embodiment.

Figure 5:
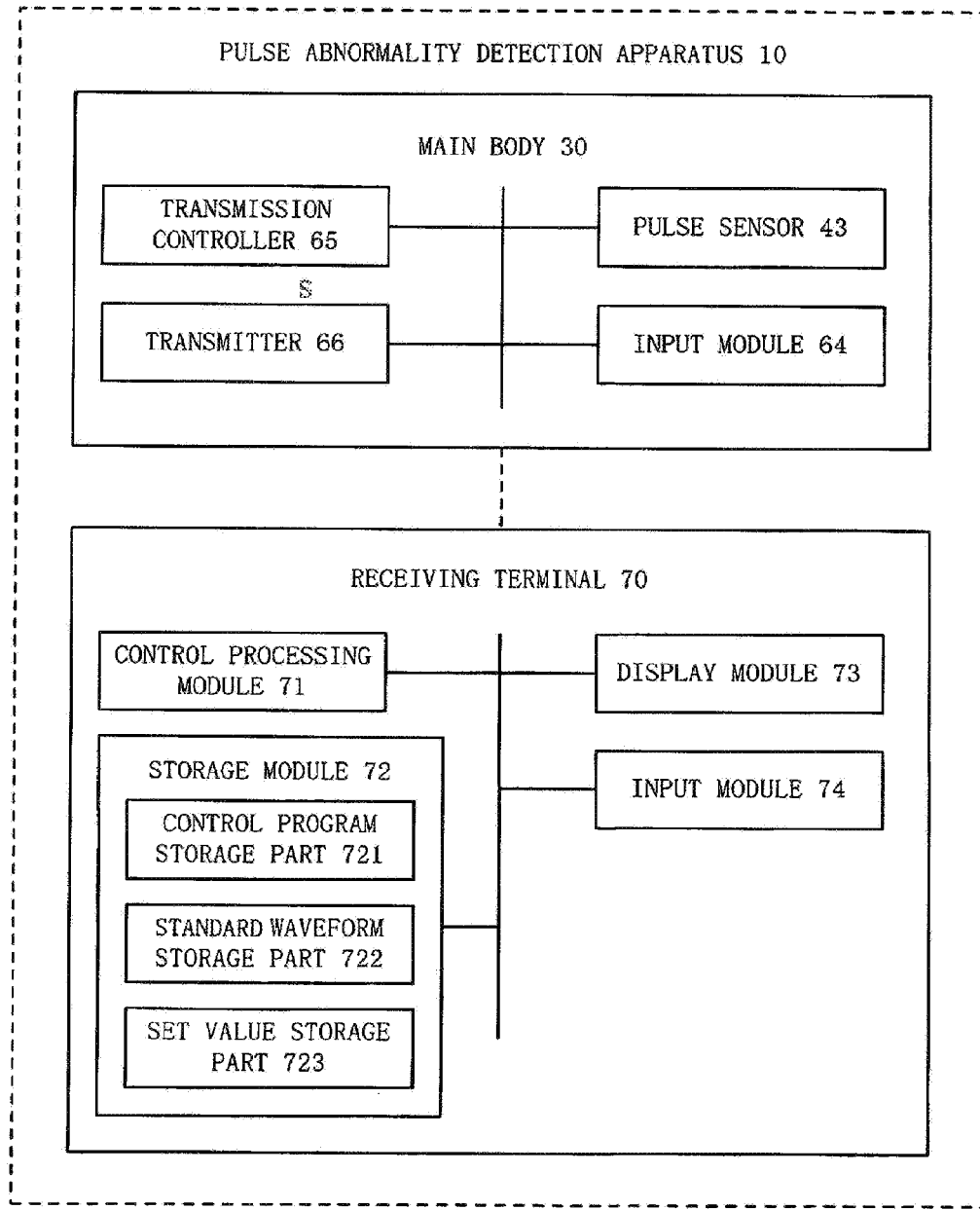
FIG. 5 is a block diagram illustrating an overall configuration of a pulse abnormality detection apparatus according to a second embodiment.

As illustrated in FIG. 5, the main body 30 has: the pulse sensor 43 provided in the sensor means 40 similar to that of the first embodiment; an input module 64 for performing an operational input on the main body 30, and for performing a driving input and a stop input on the pulse sensor 43; a transmission controller 65 for controlling a transmitting operation; and a transmitter 66 such as a wireless communication antenna. The pulse sensor 43 continuously measures pulse pressures of a radial artery B of the user, and outputs, to the transmission controller 65, an output waveform of pulses which is indicative of a temporal change in the pulse pressures. The transmission controller 65 transmits the output waveform of the pulse sensor 43 to the receiving terminal 70 via the transmitter 66.

The receiving terminal 70 includes: the control processing module 71 including a CPU, a memory, etc.; the storage module 72 including a HDD or the like; a display module 73 such as a liquid crystal display or an organic EL display; and an input module 74 including a data input part through which data to be stored in the storage module 72 is inputted, an operational input part through which an operational input is performed on the receiving terminal 70, etc. The storage module 72 has: a control program storage part 721 for storing a control program for pulse abnormality detection processing; a standard waveform storage part 722 for storing a standard pulse waveform; and a set value storage part 723 for defining a pulse allowable range for each detection item. A configuration for the standard waveform to be stored in the standard waveform storage part 722, a setting for the standard waveform in a setting mode, and usage in a use mode can be provided similarly to the first embodiment.

The control processing module 71 of the receiving terminal 70 receives and captures the pulse output waveform transmitted from the main body 30, reads, in accordance with the control program stored in the control program storage part 721, the standard pulse waveform from the standard waveform storage part 722 while reading, from the set value storage part 723, set values by which the pulse allowable range is defined, makes a comparison between the received output waveform and the standard pulse waveform, recognizes an abnormality when results of the comparison include a value falling outside the allowable range defined by the set values, and displays, on the display module 73, a detection item for which an abnormality is recognized and a message saying that an abnormality is caused. A processing structure for recognizing a pulse abnormality by the foregoing comparison is similar to that of the first embodiment.

The pulse abnormality detection apparatus 10 according to the second embodiment is capable of achieving effects similar to those of the first embodiment, except that the user can recognize a pulse abnormality on the spot in the first embodiment; in addition, the band 20 is provided with the transmitter 66, the receiving terminal 70 is provided with the pulse abnormality detector, and the output waveform from the pulse sensor 43 is transmitted to the receiving terminal 70 via the transmitter 66, thereby allowing the user himself or herself or other people such as family and doctors to recognize, on a larger display screen or the like of the receiving terminal 70, a pulse abnormality with the use of the receiving terminal 70 such as a mobile phone, an on-vehicle terminal or a personal computer, for example, for receiving data from the pulse sensor 43.

[Variations of Embodiments, Etc.]

The invention disclosed herein also includes, in addition to components of each invention or each embodiment, a variation in which these partial components are changed to other components disclosed herein and specified within an applicable range, a variation in which other components disclosed herein are added to these components and specified, or a variation formulated into a generic concept in which these partial components are eliminated and specified to the extent that partial operational effects are obtainable.

For example, in the pulse abnormality detection apparatus 10 according to the first or second embodiment, the band 20 is formed into a substantially annular shape via the main body 30; however, the band 20 itself, for example, may be formed into an annular shape, and the main body 30 may be provided so as to be put on the annular band 20. Further, in the pulse abnormality detection apparatus 10 according to the first or second embodiment, the band 20 is used by being worn around the wrist, but may have a bracelet type structure or the like, which is worn at an appropriate position of an arm. Furthermore, in the first or second embodiment, the pulse sensor 43 is formed to measure a pulse by being placed at a position corresponding to the radial artery B, but may alternatively be formed to measure a pulse by being placed at a position corresponding to an ulnar artery of the wrist. Moreover, the main body 30 is favorably formed so as to be provided with a watch panel or the like to use the apparatus also as a watch.

Besides, the pulse sensor 43 according to the first or second embodiment is formed so as to be movable between a region located inwardly of the band 20 and a region located laterally thereof so that the position of the pulse sensor 43 is adjustable, but the pulse sensor 43 may be formed so as to be movable within the region located inwardly of the band 20 or may be formed so as to be movable in the region located laterally of the band 20, for example. In addition, a temperature sensor or the like for measuring a body temperature by being placed close to the pulse sensor 43 or by being integrated into the pulse sensor 43, or another sensor such as a temperature sensor or an air pressure sensor may alternatively be provided.

Further, in the first or second embodiment, an example in which the second slide body 42 or the base plate 421 has elasticity has been described; however, an elastic member serving as a separate member may be provided between the second slide body 42 and the pulse sensor 43 by, for example, interposing a curved leaf spring between the base plate 421 of the second slide body 42 and the pulse sensor 43, for instance, and the pulse sensor 43 may be urged inwardly of the band 20 by this elastic member.

Figure 6:
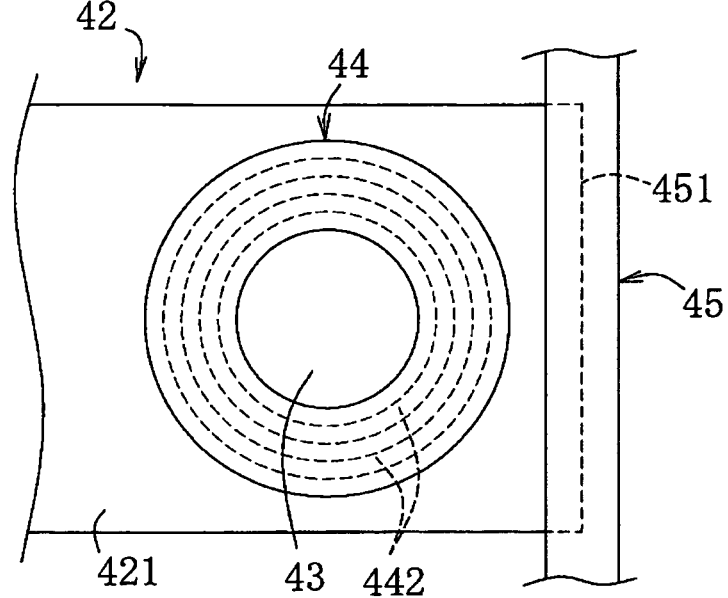
FIG. 6(a) is a bottom view illustrating a periphery of a pulse sensor of a pulse abnormality detection apparatus according to one variation.
FIG. 6(b) is a side view, partially in longitudinal cross section, of the periphery of the pulse sensor illustrated in FIG. 6(a)
FIG. 6(c) is a front view illustrating the periphery of the pulse sensor illustrated in FIG. 6(a).
Figure 6:
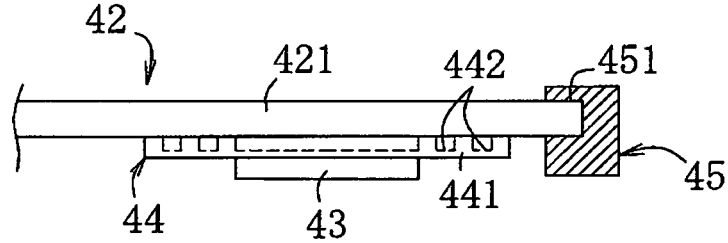
Figure 6:
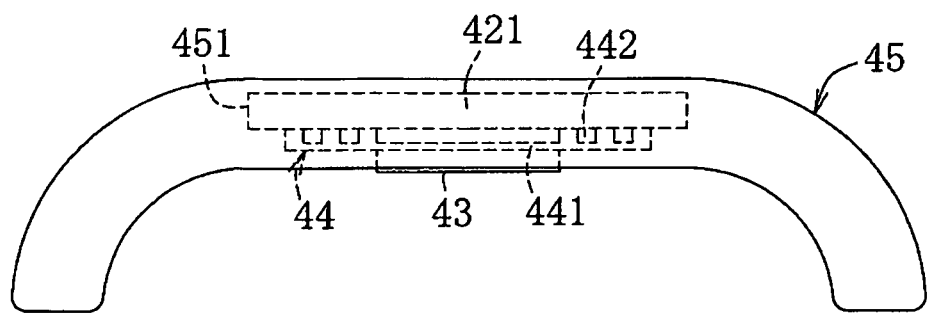

Furthermore, as illustrated in a variation of FIG. 6, a pressure sensitive diaphragm 44 may be provided as the separate elastic member. A pulse abnormality detection apparatus according to the variation of FIG. 6 is formed so that the pressure sensitive diaphragm 44 is provided on the base plate 421 of the second slide body 42, and the substantially circular pulse sensor 43 is provided at a center of the pressure sensitive diaphragm 44. The pressure sensitive diaphragm 44 is formed into a substantially circular thin plate-like shape, a plurality of concentric grooves 442 (two grooves in this example) are formed at a region of an outer periphery of a base plate 441, which is located adjacent to the base plate 421, a center portion of the base plate 441 is formed into a thin plate thinner than its peripheral region, and the pulse sensor 43 is provided at a region of the center portion, which is located opposite to the base plate 421.

A tip of the base plate 421 of the second slide body 42 illustrated in FIG. 6 is provided with a fixation member 45 that has a shape substantially conforming to at least part of a circumference of the wrist and that is formed into a substantially arcuate shape in this example. A fitted part 451 serving as a hole portion having a shape conforming to the tip of the base plate 421 is formed in a center portion of the fixation member 45, and the tip of the base plate 421 is fitted into the fitted part 451, thereby attaching the fixation member 45 to the second slide body 42.

Note that the pressure sensitive diaphragm according to the present invention is not limited to the pressure sensitive diaphragm 44 according to this example, but any other pressure sensitive diaphragm may be appropriately used within the range in which a given function is achieved. Further, when a pulse is measured at a circumference of an arm, the fixation member 45 may have a shape substantially conforming to at least part of a circumference of an arm, and the shape substantially conforming to at least part of the circumference of the wrist or that of the arm may appropriately be a substantially semicircular shape, a substantially ¾ circular shape or the like; moreover, the fixation member 45 is preferably formed by a flexible material such as flexible plastic or rubber and wound around the wrist or the like. Furthermore, the fixation member 45 may be formed by covering an outer circumference of a wire with rubber, for example, and may be bent to have a substantially elliptic shape or the like, so that the fixation member 45 is deformable into a given shape substantially conforming to at least part of the circumference of the wrist or that of the arm.

Besides, in the second embodiment, the transmission controller 65 and the transmitter 66 are formed so as to be provided in the main body 30, but the transmission controller 65 and the transmitter 66 may appropriately be formed so as to be integrated into the band 20 directly or indirectly; for example, the transmission controller 65 and the transmitter 66 may be formed so as to be provided in the sensor means 40, or the transmission controller 65 and the transmitter 66 may be formed so as to be provided in the pulse sensor 43.

Moreover, in the first embodiment, there has been described an example in which the pulse peak value interval equivalent to an R-R interval of an electrocardiogram is set as the given value obtained by a comparison made between the pulse output waveform and the standard waveform, the set upper limit value and set lower limit value of the pulse peak value interval are set as the set values by which the allowable range is defined, and an irregular pulse is set as a detection item, but the given value obtained by the waveform comparison, the set values and the detection item may be appropriately set when necessary; for example, a pulse rate measured during a given period of time may be set as the given value, a set lower limit value of a pulse rate measured during a given period of time may be set as the set value, and "Doze" may be set as the detection item. In addition, for example, a time-series pulse wave value may be detected as the given value, an autocorrelation function or ARMA (autoregressive moving average model) of a pulse wave and a permitted value or the like for the degree of consistency between a time-series pulse wave value and an autocorrelation function or ARMA may be detected as the set values, and a state of an autonomic response such as pulse wave fluctuation, pressure fluctuation or heartbeat fluctuation may be detected as the detection item.

Industrial Applicability

A pulse abnormality detection apparatus according to the present invention can be used, for example, for user's health care, prevention of drowsy driving, etc.

[Name of the Document] Drawings
[FIG. 4]
10 PULSE ABNORMALITY DETECTION APPARATUS
43 PULSE SENSOR
61 CONTROL PROCESSING MODULE
62 STORAGE MODULE
63 DISPLAY MODULE
64 INPUT MODULE
621 CONTROL PROGRAM STORAGE PART
622 STANDARD WAVEFORM STORAGE PART
623 SET VALUE STORAGE PART
[FIG. 5]
10 PULSE ABNORMALITY DETECTION APPARATUS
30 MAIN BODY
43 PULSE SENSOR
64 INPUT MODULE
65 TRANSMISSION CONTROLLER
66 TRANSMITTER
70 RECEIVING TERMINAL
71 CONTROL PROCESSING MODULE
72 STORAGE MODULE
73 DISPLAY MODULE
74 INPUT MODULE
721 CONTROL PROGRAM STORAGE PART
722 STANDARD WAVEFORM STORAGE PART
723 SET VALUE STORAGE PART

The invention claimed is:
1. A pulse abnormality detection apparatus comprising:
a band adapted and configured to be worn around a wrist or an arm;
a pulse sensor positioned under an inner face of the band and/or lateral to the band;
a pulse abnormality detector for detecting a pulse abnormality from data outputted from the pulse sensor, a first slide body that is externally attached to the band and that slides along the circumferential axis of the band; and a second slide body positioned under an inner face of the band that is slidably provided at the first slide body, wherein the second slide body slides laterally to the circumferential axis of the band and comprises the pulse sensor.

2. The pulse abnormality detection apparatus according to claim 1, the apparatus comprising:

a storage module for storing a standard pulse waveform and a set value by which a pulse allowable range is defined; and a pulse abnormality recognition module for making a comparison between an output waveform, which is data outputted from the pulse sensor, and the standard pulse waveform, and for recognizing an abnormality when results of the comparison include a value falling outside the allowable range defined by the set value, wherein the pulse abnormality detector is formed by the storage module and the pulse abnormality recognition module.

3. The pulse abnormality detection apparatus according to claim 2 further comprising:

a fixation member adapted and configured to conform to at least part of the circumference of the wrist or that of the arm or having a shape substantially conforming to at least part of a circumference of the wrist or that of the arm, the fixation member being positioned lateral to the band and comprising a slot for accepting a tip of the second slide body, thereby fixing an optimal position of the pulse sensor in a direction generally perpendicular to the circumferential axis of the band.

4. The pulse abnormality detection apparatus according to claim 2, wherein the band comprises a main body, wherein the main body comprises the pulse abnormality detector.

5. The pulse abnormality detection apparatus according to claim 2, wherein the band comprises a transmitter, and a receiving terminal comprises the pulse abnormality detector, wherein an output waveform, which is data outputted from the pulse sensor, is transmitted to the receiving terminal via the transmitter.

6. The pulse abnormality detection apparatus according to claim 1, wherein the second slide body has elasticity by which the pulse sensor protrudes away from the inner face of the band, or wherein the apparatus further comprises an elastic member provided between the second slide body and the pulse sensor, thereby allowing the pulse sensor to protrude away from the inner face of the band.

7. The pulse abnormality detection apparatus according to claim 6, wherein the elastic member is a pressure sensitive diaphragm.

8. The pulse abnormality detection apparatus according to claim 6 further comprising:

a fixation member adapted and configured to conform to at least part of the circumference of the wrist or that of the arm or having a shape substantially conforming to at least part of a circumference of the wrist or that of the arm, the fixation member being positioned lateral to the band and comprising a slot for accepting a tip of the second slide body, thereby fixing an optimal position of the pulse sensor in a direction generally perpendicular to the circumferential axis of the band.

9. The pulse abnormality detection apparatus according to claim 6, wherein the band comprises a main body, wherein the main body comprises the pulse abnormality detector.

10. The pulse abnormality detection apparatus according to claim 1 further comprising:

a fixation member adapted and configured to conform to at least part of the circumference of the wrist or that of the arm or having a shape substantially conforming to at least part of a circumference of the wrist or that of the arm, the fixation member being positioned lateral to the band and comprising a slot for accepting a tip of the second slide body, thereby fixing an optimal position of the pulse sensor in a direction generally perpendicular to the circumferential axis of the band.

11. The pulse abnormality detection apparatus according to claim 1, wherein the band comprises a main body, wherein the main body comprises the pulse abnormality detector.

12. The pulse abnormality detection apparatus according to claim 1, wherein the band comprises a transmitter, and a receiving terminal comprises the pulse abnormality detector, wherein an output waveform, which is data outputted from the pulse sensor, is transmitted to the receiving terminal via the transmitter.

13. The pulse abnormality detection apparatus according to claim 12, wherein the transmitter is a connection line.

14. The pulse abnormality detection apparatus according to claim 5, wherein the transmitter is a connection line.

15. The pulse abnormality detection apparatus according to claim 1, wherein the band comprises a temperature sensor or an air pressure sensor.

* * * * *